United States Patent [19]

Meiffren et al.

[11] Patent Number: 5,424,639

[45] Date of Patent: Jun. 13, 1995

[54] SUPPORT DEVICE FOR A PROBE FOR THE DETECTION AND LOCATION OF POSSIBLE FAULTS WITHIN A BORE

[75] Inventors: Jean-Luc Meiffren, Saint Germain les Corbeil; José C. J. Robin, Voisins le Bretonneux, both of France

[73] Assignee: Societe Nationale d'Etude et de Construction de Moteurs d'Aviation "SNECMA", Paris, France

[21] Appl. No.: 134,906

[22] Filed: Oct. 13, 1993

[30] Foreign Application Priority Data

Oct. 14, 1992 [FR] France ................. 92 12244

[51] Int. Cl.⁶ ................. G01N 27/90; G01N 37/00
[52] U.S. Cl. ................. 324/219; 73/661; 33/542; 324/262
[58] Field of Search ................. 324/219, 220, 221, 226, 324/262; 73/623, 660, 661; 33/542

[56] References Cited

U.S. PATENT DOCUMENTS 3,831,084  8/1974  Scalese et al. .
4,142,154  2/1979  Couchman .
4,219,774  8/1980  Rogel et al. ................. 324/262
4,454,473  6/1984  Rosauer ................. 324/262

FOREIGN PATENT DOCUMENTS 0095845  12/1983  European Pat. Off. .
0461763  12/1991  European Pat. Off. .
2492527   4/1982  France .
2543686  10/1984  France .

*Primary Examiner*—Gerard R. Strecker
*Attorney, Agent, or Firm*—Oblon, Spivak, McClelland, Maier, & Neustadt

[57] ABSTRACT

A support device for a probe for the detection and location of possible faults within a bore. The device forms a simple structure enabling a nonspecialized operator to perform reproducible measurements. The device incorporates a probe-holding spindle equipped at one end thereof with a mechanism for fixing a measuring probe and a spindle support having a longitudinal guidance mechanism for the spindle and a mechanism for angular positioning thereof. The device makes it possible to inspect the bores of a rotor shaft.

11 Claims, 1 Drawing Sheet

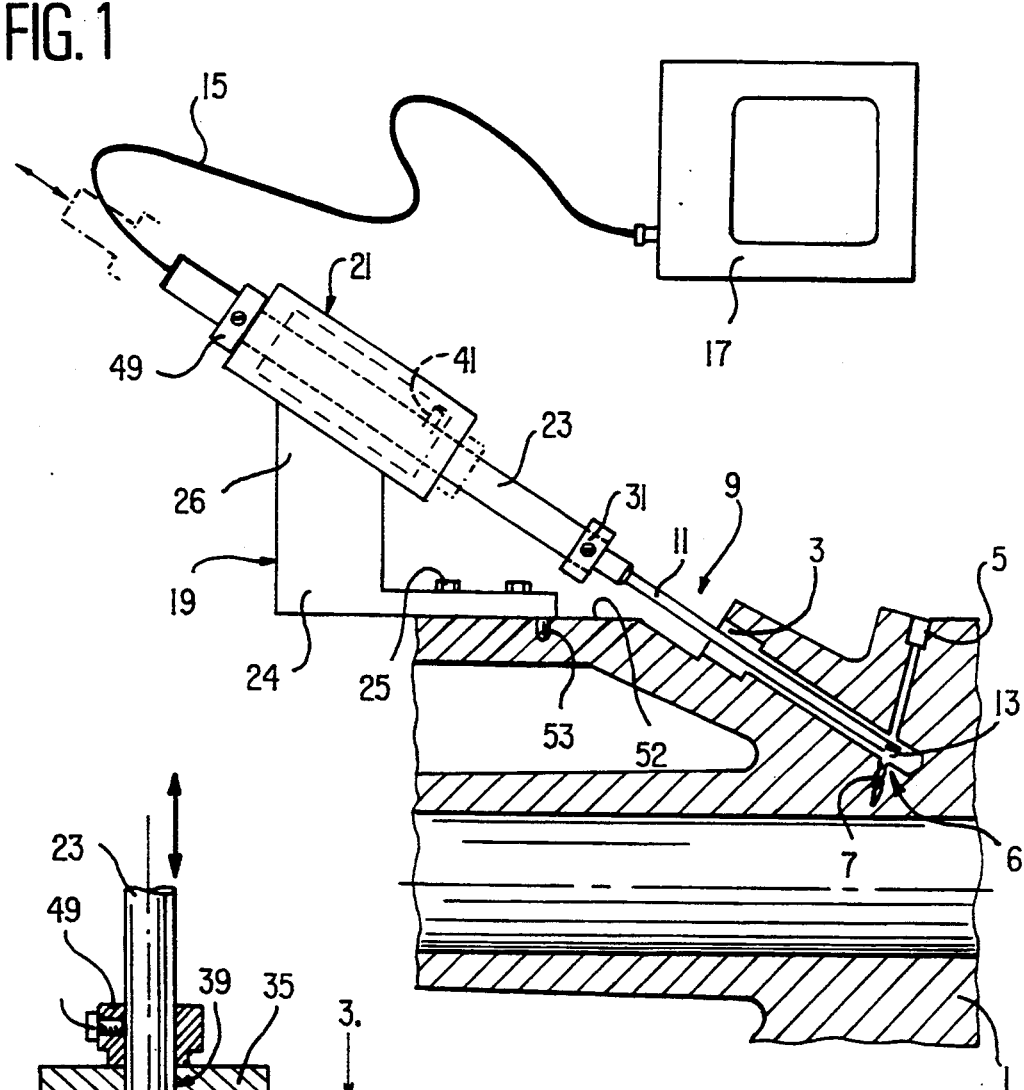
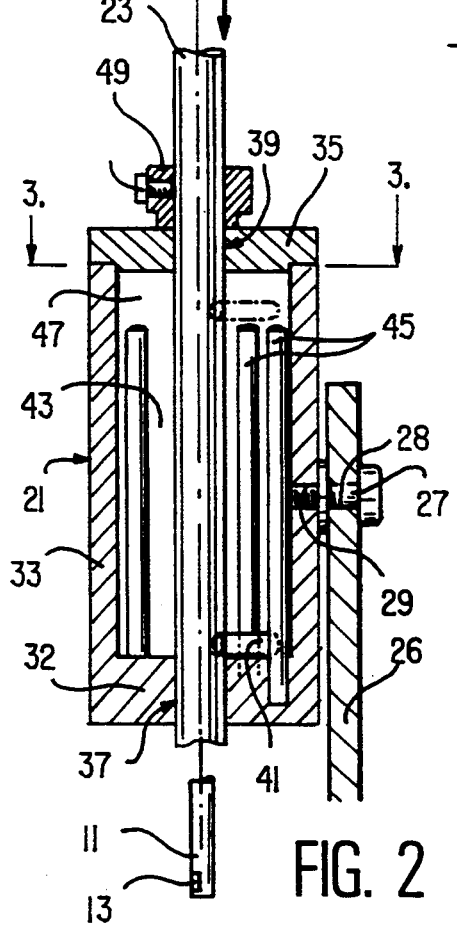
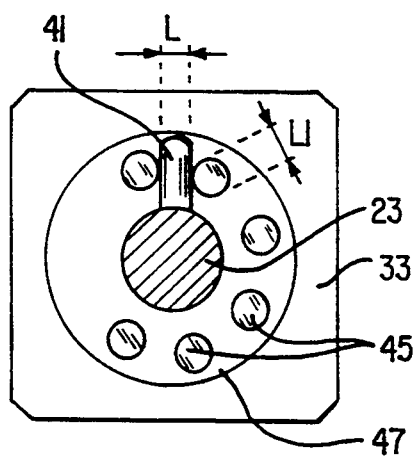
FIG. 1
FIG. 2
FIG. 3

SUPPORT DEVICE FOR A PROBE FOR THE DETECTION AND LOCATION OF POSSIBLE FAULTS WITHIN A BORE

BACKGROUND OF THE INVENTION

1. Field of the invention

The present invention relates to a support device for a probe for the detection and location of possible faults within a bore.

2. Discussion of the Background

Incidents which have occurred in flight by both aircraft and helicopters have revealed that cracks appear in a particularly inaccessible area of the rotor shaft and more specifically at the intersection of two small diameter, internal lubricating ducts. These cracks, initiated during the operation of the aircraft can give rise to the shaft fracturing, engine loss and even to the crashing of the aircraft. It is therefore important during equipment inspection and maintenance operations to check whether such cracks are being formed.

Several inspection methods have been envisaged, including magnetoscopy. This method consists of spraying the part to be inspected with a liquid containing metal particles and subjecting the same to a magnetic field. If there is a crack in the part, an easily measurable stray field then appears. However, this method only makes it possible to detect faults and defects when they have assumed considerable dimensions, i.e. much too late in order to comply with safety requirements.

The aim has therefore been to develop a device for the inspection of parts permitting a particularly early and reliable detection of possible faults. This device is applicable in general terms to the early detection of cracks appearing within a small size bore and which are therefore difficult of access, no matter whether the bore occurs on a rotor shaft or any other mechanical part.

The proposed solution makes use of a probe, more particularly an eddy current inspection probe. This probe constitutes a portable equipment and which is therefore very practical, because it can be used directly at the part inspection location. Moreover, this inspection procedure is reliable. However, it would be desirable to be able to carry out reproducible inspections or checks on the same part and on all the parts of the same batch or series. To this end, it would be desirable to have a support device for the probe permitting the displacement of the latter with respect to the part to be inspected in accordance with predetermined, precise positions.

The prior art already discloses several devices using an eddy current probe for checking a certain number of mechanical parts. Thus, FR-A-2 543 686 describes a support device for an eddy current probe making it possible to place the latter in several predetermined positions with respect to a surface to be analyzed. This support device is specifically designed for the analysis of the external surface of a part and in particular a portion of a rotor, but cannot be used for positioning an eddy current probe within a bore.

FR-A-2 492 527 describes a positioning block for an eddy current inspection probe, said block being positionable on the blade of a turbomachine. For the same reasons as those given hereinbefore, it cannot be used for the inspection of small diameter bores.

U.S. Pat. No. 4,142,154 also discloses a probe for an eddy current inspection probe making it possible to carry out measurements within a bore. The probe used is covered with a protective sleeve. The support is provided with a screw thread actuated by a motor permitting the displacement of said probe in translation within the bore to be inspected. This support also comprises a gear and a motor permitting the rotation of the probe on itself within the bore. However, this device has a complex construction and requires the use of two motors and is therefore complicated to manufacture.

Finally, EP-A-95 845 discloses an inspection apparatus using an eddy current probe for carrying out measurements within a bore. This apparatus has a variable diameter sleeve within which the probe is installed. The apparatus can be manually lowered within the bore to be inspected and a motor rotates the probe on itself.

It should be noted that most of the existing probe-holding devices make use of a motor for the displacements of the probe and consequently have a complex structure.

SUMMARY OF THE INVENTION

The object of the invention is to provide a probe support device having a simple structure and which is easy to use, so that it is possible to carry out a longitudinal scan of the wall of the bore to be inspected with an angular incrementation of the probe.

A further object of the invention is to provide a probe support device making it possible to rapidly make reproducible measurements on a series of identical parts whereby this can be carried out by an nonspecial operator.

The invention also has as a further object the provision of a probe support device especially designed for the displacement of a probe within a bore, whose axis is oblique with respect to the face or the major axis of the part in which it is provided.

The invention therefore relates to a device for supporting a probe for the detection and location of possible faults within a bore having a probe-holding spindle with, at one of its ends, means for fixing the said probe and a spindle support having means for the longitudinal guidance of said spindle and means for the angular positioning thereof.

According to the features of the invention, the spindle support comprises at least one positioning base to which is fixed a plate perforated by a guide orifice through which said spindle can slide. The probe-holding spindle also comprises at least one pin extending radially from its outer surface and said plate is provided with at least two guide rods arranged around the guide orifice and extending parallel to the axis of said orifice, said reds being spaced from one another by a distance substantially corresponding to the width of the pin, so that the latter can slide between them, said pin and said rods cooperating so as to form longitudinal guidance means.

Advantageously, said device comprises at least three guide rods and the pin and said rods cooperate to form the angular positioning means for the spindle.

The probe-support device ensures the strict positioning of the probe, i.e. its centring and its angular indexing. It also makes it possible to scan the area of the bore to be inspected under good reproducibility and reliability conditions. This device associated with a sensitive probe makes it possible to detect cracks having dimensions as small as 1.5 mm long and 0.8 mm deep, i.e. virtually as soon as they appear.

BRIEF DESCRIPTION OF THE DRAWINGS

The invention is described in greater detail hereinafter relative to a non-limitative embodiment and with reference to the attached drawings, wherein as shown:

FIG. 1 is a diagrammatic view of the probe support device according to the invention during operation.

FIG. 2 is a partially sectional view of a portion of the device according to the invention.

FIG. 3 is a sectional view taken along line 3—3 of FIG. 2.

As has been stated hereinbefore, said support device and the probe are used in maintenance, particularly for detecting cracks on a part of the driving shaft type, in areas which are difficult to access such as the intersection of a bore and a relatively small diameter hole.

In the special case illustrated in FIG. 1, the part 1 to be inspected is a rotor shaft having two lubricating bores 3 and 5 respectively with a diameter of 4.3 and 1.9 mm. It is readily apparent that these bores, quite apart from their small dimensions, are difficult to inspect even using endoscopic methods. When cracks are initiated, they are generally formed on that portion 6 of the inner wall of the bore 3 facing the bore 5. Obviously, it is clear that this device can be used for inspecting any random mechanical part having at least one bore within which a crack 7 is liable to form.

The probe used in the embodiment of the invention is advantageously an eddy current inspection probe, but it could also be any other random probe type. This probe 9 comprises a rod 11 at the end of which is provided the actual sensor 13. The latter is placed on the side wall of the rod 11, as can best be seen in FIG. 2. At its other end the rod 11 is extended by a cable 15 connected to an oscilloscope 17 permitting the performance of measurements. The operation and structure of said inspection probe are of a conventional nature and will not be described further here.

The probe support device according to the invention mainly comprises a positioning base 19, a casing 21 and a probe-holding spindle 23.

Advantageously, the positioning base 19 is L-shaped. It is constituted by a planar support 24 and a flange 26 perpendicular to said support 24 and to which the casing 21 is fixed. The planar support 24 can advantageously be fixed to the part 1 to be inspected by means of bolts 25.

Preferably and as illustrated in FIG. 2, said casing 21 is fixed to the flange 26 by means 27 allowing an angular displacement of said casing 21 with respect to the flange 26. According to an embodiment of the invention, said means 27 are constituted by a screw. In this case, a bore 28 and a tapped bore 29 are respectively provided on the flange 26 and on one of the walls of the casing 21.

As is illustrated in FIG. 1, the probe-holding spindle 23 is provided at one of its ends with a mandrel 31 making it possible to ensure the fixing of the probe 9 and more particularly the rod 11. In a conventional manner, said mandrel 31 incorporates a collet. The probe-holding spindle 23 is hollow, so as to permit the passage of the cable 15.

As illustrated in FIG. 2, the casing 21 comprises a plate 32 forming the bottom, side walls 33 and a plate 35 forming the top. According to a preferred embodiment of the invention and as illustrated in FIGS. 2 and 3, said casing is shaped like a rectangular parallelepiped. The plate forming the bottom 32 and the plate forming the top 35 are respectively perforated with a guide orifice 37, 39 permitting the passage of the probe-holding spindle 23, which can therefore slide within the casing 21.

On its outer surface the probe-holding spindle 23 has at least one stud or pin 41 extending radially with respect to the longitudinal axis of said spindle. This pin 41 is located on the spindle portion within the enclosure 43 defined by the casing 21. Preferably the enclosure 43 is cylindrical. In addition, the casing 21 is provided with at least two guide rods 45 extending from the plate forming the bottom 32, parallel to the longitudinal axis of the guide orifice 37. These guide rods 45 are located around the orifice 37 and are spaced from one another by a distance substantially corresponding to the width L of the pin 41, so that the latter can slide between them without rubbing, but while still being held (cf. FIG. 3). Said pin 41 and said guide rods 45 cooperate so as to form longitudinal guidance means for the probe-holding spindle 23. In addition, the guide rods 45 prevent the spindle 23 from rotating on itself, because the rotation of the latter is limited by the pin 41.

However, in a preferred manner, the casing 21 has at least three guide rods 45 and advantageously, as illustrated in FIG. 3, has six such rods. The guide rods 45 do not extend over the entire height of the enclosure 43, so as to define a displacement space 47, whose function will be described hereinafter.

The probe-holding spindle 23 is also provided with an end of travel stop 49 located on that portion of the spindle positioned outside the casing 21. Preferably, said stop 49 is annular and surrounds the spindle 23. It is fixed to the latter by means of a screw 51, which thus constitutes a means for the longitudinal positioning of said stop along the spindle 23. It is therefore possible to adjust the travel of the probe-holding spindle 23 within the casing 21.

It should be noted that in a simplified embodiment of the invention, the side walls 3 and the plate 35 forming the cover of the casing 21 can be eliminated. The probe-holding spindle 23 is then only maintained and guided by the rods 45 and by the guide orifice 37. The plate 32 is then directly fixed to the flange 26 of the base 19.

In a third embodiment of the invention, only the plate forming the top or cover 35 is retained and the walls 33 and plate 32 are eliminated. In this case, the plate forming the top 35 is fixed to the positioning base 19 and supports the guide rods 45.

The operation of the support device for the probe will now be described in greater detail relative to the drawings. The user introduces the probe 9 into the probe-holding spindle 23, in such a way that the rod 11 projects from said spindle and the cable 15 passes out of the end of the latter. He then tightens the mandrel 31 so as to lock the rod 11.

He also fixes the positioning base 19 by means of the screws 25 to a control part to be inspected. This control part is not shown in FIG. 1, but it is identical to the part 1. It also incorporates a control crack made by electro-erosion and which simulates the real crack. This control crack has an approximate depth of 1.5 mm and an approximate width of 0.8 mm, which essentially corresponds to the smallest cracks which can be detected by the probe 9. This control part is used for calibrating the oscilloscope 17 and regulating the displacement of the probe 9 and the probe-holding spindle 23.

The user can then regulate the oscilloscope 17, so as to be able to perform measurements with the probe 9. He can then manually slide the probe-holding spindle 23 towards the interior of the bore 3 of the control part, so that the sensor 13 traverses the entire length of one of the generatrixes of said bore 3. When the probe essentially reaches the bottom of the bore, the user regulates the position of the end of travel stop 49 by means of the screw 51. Thus, in subsequent measurements, he can without risk more rapidly manipulate the probe-holding spindle 23, without the probe 9 touching the bottom of the bore 3. He also screws the screw 27 up, so as to adapt the angle between the casing 21 and the planar support 24 to the angle formed by the bore 3 with the plane 52 of the part 1 on which the positioning base 19 is fixed.

Then, the user adapts the probe support device to the part to be inspected 1. In order to facilitate this manipulation, it is possible to provide on the base 19 and more particularly on the planar support 24, a locating member 53 designed to cooperate with an orifice on the part 1. He then performs a first measurement by sliding the probe-holding spindle 23 until the rod 11 is substantially at the bottom of the bore 3 to be inspected. During this operation, the pin 41 cooperating with the guide rods 45 makes it possible to guide the spindle 23 in translation. When the user wishes to carry out a second measurement, he raises the spindle 23 so as to bring the sensor 13 of the probe 9 to the entrance of the orifice 3 to be inspected. At the same time he brings the pin 41 into the displacement space 47 of the casing 21 and can then pivot the probe-holding spindle 23, because the rotary movement of the pin 41 is no longer limited by the rods 45 (position shown in FIG. 2). He then engages the pin 41 between the two continuous guide rods 45 and again completely lowers the spindle 23 into the casing 21.

Advantageously, the probe 9 is placed within the probe support device in such a way that the sensor 13 scans the entire portion 6 of the inner wall of the bore 3 facing the bore 5. In other words, the rod 11 is placed in the probe-holding spindle 23, so that the five angular positions authorized by the six guide rods 45 make it possible to inspect the indicated zone.

It is clear that the number of guide rods 45 is a function of the angular surface which it is wished to scan with the probe 4. This number is at least three if it is wished to have a possibility of a choice between two defined angular positions. In addition, the width L of the pin 41 and the width $L_1$ of the rods 45 could be adapted as a function of the value of the desired angular variation between two consecutive measurements.

By means of the probe support device, even an untrained technician can easily perform measurements by manually displacing the probe in accordance with a certain number of predetermined positions.

Obviously, numerous modifications and variations of the present invention are possible in light of the above teachings. It is therefore to be understood that within the scope of the appended claims, the invention may be practiced otherwise than as specifically described herein.

We claim:

1. Support device for a probe for the detection and location of faults within a bore, incorporating a probe-holding spindle having at one end thereof a mechanism fixing said probe and a spindle support having a mechanism longitudinal guiding said spindle and angularly positioning the spindle, wherein the spindle support device comprises:
   at least one positioning base;
   a plate fixed to the base and having a guidance orifice through which the spindle is slidable, wherein the probe-holding spindle has at least one pin extending radially from an outer surface thereof and wherein the plate is provided with at least two guide rods located around the guide orifice and extending parallel to the longitudinal axis of said orifice, said at least two rods being spaced from one another by a distance substantially corresponding to at least a width dimension of the pin so that the pin is slidable between the two rods, said pin and said two rods cooperating so as to form a longitudinal guidance mechanism.

2. Support device for a probe for the detection and location of faults within a bore, incorporating a probe-holding spindle having at one end thereof a mechanism fixing said probe and a spindle support having a mechanism longitudinally guiding the spindle and angularly positioning the spindle, wherein the support device comprises:
   at least one positioning base;
   a casing having side walls, a first plate forming a bottom portion of the casing and a second plate forming a top portion of the casing, one of said first and second plates having a guidance orifice formed therein through which the spindle is slidable;
   the probe-holding spindle having at least one pin extending radially from an outer surface thereof wherein the first and second plates are provided with at least two guide rods located around the guide orifice and extending parallel to the longitudinal axis of the orifice, said at least two rods being spaced from one another by a distance substantially corresponding to a width dimension of the pin so that the pin is slidable between said at least two guide rods, said pin and said at least two guide rods cooperating so as to form a longitudinal guidance mechanism and wherein the guide rods extend within the enclosure defined by the casing.

3. Probe support device according to claims 1 or 2, wherein the at least two guide rods comprise at least three guide rods and the pin and the said rods cooperate to form said angular positioning mechanism for said probe-holding spindle.

4. Probe support device according to claim 2, wherein the guide rods extend over only a portion of a length dimension of the casing so as to define a displacement space within which the pin can pivot in angular manner.

5. Probe support device according to claim 1, wherein the mechanism fixing the probe to the spindle includes a mandrel.

6. Probe support device according to claims 1 or 2, wherein the probe-holding spindle includes an end of travel stop placed on a side wall thereof and at an end portion of the enclosure defined by the casing.

7. Probe support device according to claim 6, wherein the end of travel stop includes a longitudinal positioning mechanism which is movable along said probe-holding spindle.

8. Probe support device according to claim 1, wherein the plate is fixed to the positioning base by an angular displacement mechanism which adjusts angular displacement of said plate with respect to the base.

9. Probe support device according to claims 1, or 2, wherein the positioning base has at least one locating member which positions the probe with respect to the bore to be inspected.

10. Probe support device according to claims 1 or 2, wherein the probe comprises an eddy current inspection probe.

11. Probe supporting device according to claim 2, which comprises an angular displacement mechanism which adjusts angular displacement of said one of said first and second plates with respect to the base wherein at least one of the first and second plates is fixed to the positioning base by said angular displacement mechanism.

* * * * *